Figure 1:
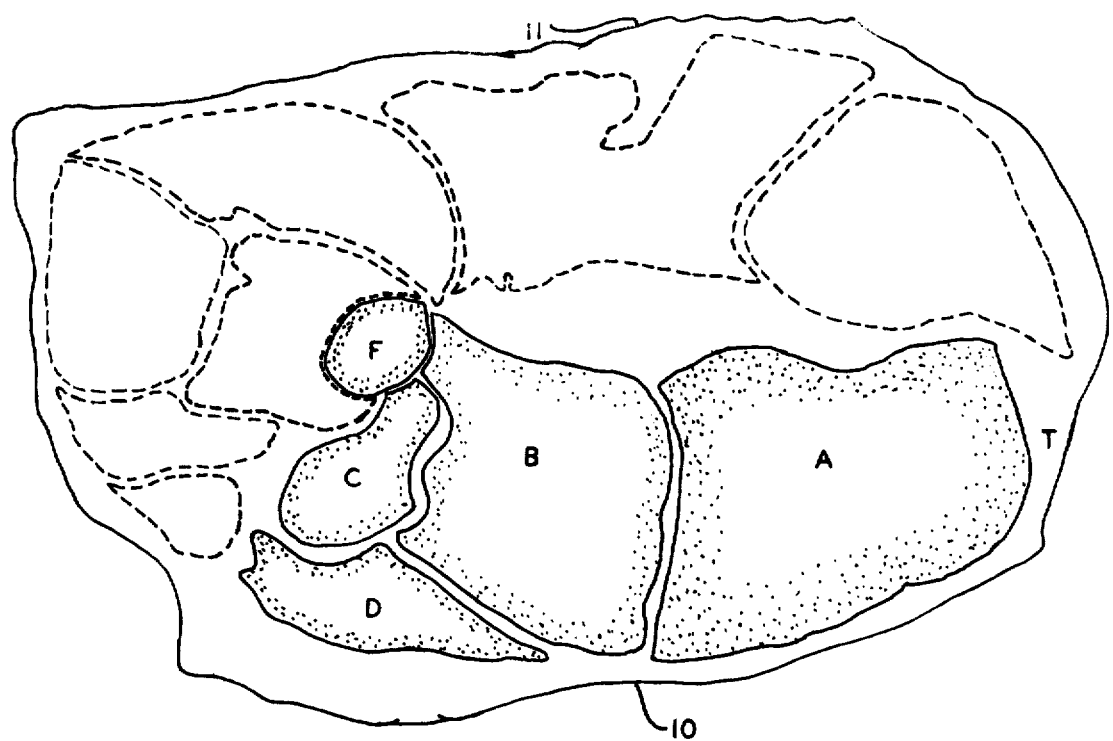

United States Patent

Kammlah et al.

[11] 4,052,890
[45] Oct. 11, 1977

[54] MEASURING THE TENDERNESS OF COOKED BEEF

[75] Inventors: Henry W. Kammlah, Scottsdale; Harold K. Herring, Paradise Valley, both of Ariz.; Duane E. Koch, Jefferson, Wis.

[73] Assignee: Armour and Company, Phoenix, Ariz.

[21] Appl. No.: 658,888

[22] Filed: Feb. 18, 1976

[51] Int. Cl.² ............................................. G01N 3/42
[52] U.S. Cl. ...................................................... 73/81
[58] Field of Search ............................................. 73/81

[56] References Cited

U.S. PATENT DOCUMENTS 3,602,038  8/1971  Hansen ............................. 73/81

Primary Examiner—James J. Gill
Attorney, Agent, or Firm—Frank T. Barber; Carl C. Batz

[57] ABSTRACT

A method for testing cooked beef rounds to determine their tenderness by pressing a pointed probe into that portion of the Semimembranosus muscle of a cooked round which is proximal to the rump roast, and measuring the force required to penetrate the muscle to a predetermined depth.

3 Claims, 2 Drawing Figures

MEASURING THE TENDERNESS OF COOKED BEEF

This invention relates to the determination of tenderness of cooked beef. More particularly the invention relates to the making of such determination in a way which does not destroy the meat being tested but permits the meat to be marketed and consumed in the regular channels.

BACKGROUND

A large amount of research work has been done to develop methods and apparatus for testing raw meat to determine its tenderness when cooked, and some of these methods have proved to be quite accurate. For example, good results have been obtained in the testing of raw meat according to the teachings of U.S. Pat. Nos. 3,593,572, 3,602,038, 3,636,757 and 3,688,566, and there is disclosed particularly in U.S. Pat. No. 3,732,727 a portable probe device which is equipped with means for measuring the force necessary to make a prescribed insertion of the probes.

Although the testing of raw meat to determine its tenderness when cooked has been well developed, there are occasions in the meat packing industry when it would be desirable to test cooked meat for tenderness, but the methods heretofore available for this have been notably inaccurate and not of a dependable nature. In the past, such measurements have been shown to have poor correlation with shear tests made on meat from the same animal, and there has been a need for more reliable, non-destructive methods for determining the tenderness of cooked meat, particularly cooked beef.

SUMMARY

Using a cooked beef round we have discovered that by pressing a pointed probe into the end of the Semimembranosus, which is proximal to the rump roast, the force required is an accurate measurement of the tenderness of the cooked meat, and our improved method of testing of cooked beef for tenderness involves the insertion of a probe into this portion of this particular muscle while measuring the force required to make the insertion. Preferably, we take account of the maximum force necessary to insert the probe to a predetermined depth in the meat.

DESCRIPTION

Figure 2:
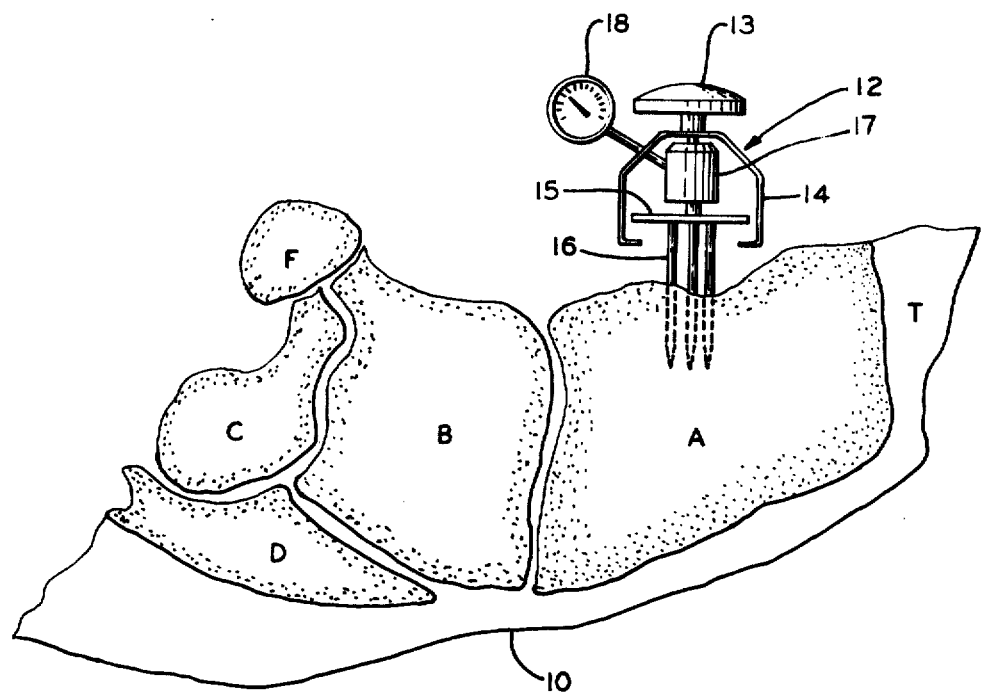

In this specification we described the preferred mode of practicing the invention and include for purposes of illustration the accompanying drawing in which:

FIG. 1 is a schematic cross-sectional view of a round of beef showing the location of the Semimembranosus muscle; and FIG. 2 is a partial-sectional view similar to FIG. 1 but with muscles on the outside of the round deleted and showing insertion of probes into the Semimembranosus muscle.

As illustrated, F. designates the femur bone; A designates the Semimembranosus muscle; B is the adductor muscle; C is the pectineus muscle; D is the gracilis muscle; and T is layer of animal fat. The dotted lines in FIG. 1 are the outline of the other muscles in the round not directly involved in this invention.

Each round has an outside and an inside corresponding to its position on the body of the animal. As illustrated in FIG. 1 the inside round includes muscles A and B whereas the outside round includes muscles E and G and F in the femur bone.

In our process, the meat round is cooked in the usual way and the Semimembranosus muscle A is removed from the round or at least is exposed by removal of the meat on one side of this muscle. As shown in FIG. 2 the probe device 12, similar to the device described in detail in U.S. Pat. No. 3,602,038, is inserted into the muscle A. Device 12 includes a handle 13, and a frame 14 of inverted U-shape. The plate 15 has depending therefrom the pointed probe 16. As shown, the probes are about 2.5 inches long, $\frac{1}{8}$ inch in diameter and have tapered end portions with pointed tips. In our process the pointed tips have been found to yield greater accuracy when compared with the blunt tips which have edges which tend to cut or tear the meat rather than just push it aside.

The device 12 includes a transducer 17 which translates pressure exerted on probe 16 to electrical values which are indicated on dial 18. In use, this device is lowered to press probe 16 down into the meat muscle until the frame 14 comes into contact with the surface of the meat. This causes the probes to be inserted to a predetermined depth. The reading on the dial 18 is a measure of the tenderness of the meat with the lower values indicating greater tenderness. Readings of the maximum force required during the penetration of the probes are the most reliable and it is immaterial whether this maximum force be during the first or the later part of the penetration.

The Semimembranosus muscle A (as shown in cross-section in FIGS. 1 and 2) is of the order of about 8 to 10 inches long in a mature beef animal. It may be regarded as having a proximal end, this being the upper end nearest the rump roast, and a distal end, which is the lower end which is farthest from the rump roast. For convenience we call the upper one-half of this muscle the proximal portion and the lower one-half the distal portion. According to our method, the injection of the probes to determine tenderness of the cooked beef should be made in the proximal portion.

To demonstrate the practice of our process, to evaluate the results obtained, and to compare the results with other processes, a number of tests were made which are recorded in the following examples.

EXAMPLE I

Twenty inside rounds were purchased from a brokerage house in Chicago. Eight of these rounds were U.S.-D.A. Choice grade and twelve were U.S.D.A. Good grade. The Semimembranosus muscle was removed from adjoining muscles and placed in a plastic bag, vacuum sealed, placed in a water bath (200° F.) and cooked to an internal temperature of 170° F. The Semimembranosus muscle was cooled inside the bag to an internal temperature of 95° F. The bag was opened and the Semimembranosus muscle probed at the proximal and distal portions near their respective ends of the muscle, using the probing device described in U.S. Pat. No. 3,602,038. The probes were $\frac{1}{8}$ inch in diameter and tapered to a point at their ends at a rate of 1/16 inch per inch needle length. This brings a point at 1 inch of taper. Then one 2-inch slice was removed from the proximal and distal portions of the Semimembranosus muscle by cutting across the fibers near the areas probed by the probing device. Six cores 1 inch in diameter (parallel to fiber direction) were removed and when they had reached a temperature of 80° F were sheared three times using a Warner Bratzler Shear attached to an Instron Universal Testing instrument, and the peak force was recorded using the average score of the six cores.

In the following Table No. I, we give the values obtained from each cooked round tested according to our probing test using sharp probes, and according to the Warner Bratzler Shear test both as to the proximal and distal end portions of the Semimembranosus muscle.

TABLE I

| Round* No. | Probing Test (lb.) | | Warner Bratzler Shear (lb.) | |
|---|---|---|---|---|
| | Proximal | Distal | Proximal | Distal |
| 1 | 32.0 | 29.0 | 11.5 | 21.9 |
| 2 | 42.0 | 37.0 | 14.3 | 18.7 |
| 3 | 45.5 | 40.0 | 14.6 | 20.7 |
| 4 | 42.0 | 35.0 | 15.1 | 19.1 |
| 5 | 44.0 | 43.0 | 19.4 | 21.2 |
| 6 | 50.0 | 38.0 | 18.2 | 22.0 |
| 7 | 48.0 | 40.0 | 19.7 | 20.3 |
| 8 | 43.0 | 34.0 | 17.7 | 20.3 |
| 9 | 42.5 | 35.5 | 17.4 | 21.0 |
| 10 | 38.0 | 36.0 | 14.0 | 20.2 |
| 11 | 50.0 | 35.0 | 20.5 | 24.1 |
| 12 | 49.5 | 39.0 | 16.5 | 22.5 |
| 13 | 30.5 | 28.0 | 16.2 | 24.1 |
| 14 | 39.5 | 36.0 | 15.1 | 17.2 |
| 15 | 38.0 | 34.0 | 14.9 | 23.6 |
| 16 | 43.0 | 38.0 | 16.4 | 17.3 |
| 17 | 47.0 | 40.0 | 16.2 | 19.7 |
| 18 | 44.0 | 42.0 | 16.6 | 25.8 |
| 19 | 42.5 | 31.0 | 13.8 | 19.4 |
| 20 | 46.5 | 38.5 | 16.5 | 23.2 |

*1 – 8 U.S.D.A. Choice grade
9 – 20 U.S.D.A. Good grade

According to our calculations using the values of Table I it is found that there is an overall correlation of 0.62 between the values of the probing test and the Warner Bratzler Shear test for the proximal portion, which we regard as quite good, but a correlation of only −0.04 between the values of the probing test and the Warner Bratzler Shear test for the distal portion, which we regard as very poor.

EXAMPLE II

At the same time as data of Table I was obtained we also tried substituting needles with blunt ends and obtained the values from the probe test as reported in the following Table II.

TABLE II

| Round No. | Probe Test | |
|---|---|---|
| | Proximal | Distal |
| 1 | 29.0 | 24.0 |
| 2 | 41.5 | 34.0 |
| 3 | 44.0 | 38.5 |
| 4 | 42.0 | 35.0 |
| 5 | 36.0 | 33.0 |
| 6 | 45.0 | 40.0 |
| 7 | 35.5 | 37.0 |
| 8 | 39.5 | 34.0 |
| 9 | 39.0 | 35.0 |
| 10 | 42.5 | 36.0 |
| 11 | 45.0 | 43.0 |
| 12 | 46.0 | 43.0 |
| 13 | 41.0 | 38.0 |
| 14 | 42.0 | 44.5 |
| 15 | 38.0 | 40.0 |
| 16 | 48.5 | 43.5 |
| 17 | 49.0 | 42.0 |
| 18 | 43.0 | 41.0 |
| 19 | 45.0 | 42.0 |
| 20 | 45.5 | 47.0 |

Comparing values of Table II with values obtained by the Warner-Bratzler Shear tests given in Table I, statistical analysis gives the correlation of 0.26 for the proximal portion and 0.04 for the distal portion, neither of which is considered a very good correlation, but the correlation between the distal values must be considered very poor.

These tests therefore bring us to the conclusion that of the non-destructive type tests the probe test taken at the proximal portion of the Semimembranosus muscle and using the pointed probe give the most reliable values. It is, of course, to be understood that by the term "pointed probe" the point need not be ultra sharp, however, the tip of the needle should come to a point rather than be blunt.

While we have described our invention principally in connection with one embodiment thereof, it will be apparent to those skilled in this art that other embodiments may be utilized and many changes may be made all within the spirit of the invention and the scope of the appended claims.

We claim:

1. In a process for determining the tenderness of cooked rounds of beef, the steps of pressing a pointed probe into the proximal end portion of the Semimembranosus muscle of cooked beef to a pedetermined depth, and measuring the maximum force of penetration.

2. A process as set forth in claim 1 in which a plurality of said probes are pressed into said portion of said muscle and the maximum combined force of penetration of all said probes is measured.

3. A process as set forth in claim 1 in which said probe is pressed into the side of said muscle portion.

* * * * *